United States Patent [19]

Winslow

[11] Patent Number: 4,895,257

[45] Date of Patent: Jan. 23, 1990

[54] CONTAINER SYSTEM FOR DISPENSING PHARMACEUTICAL PRESCRIPTION TO VISUALLY OR MEDICALLY IMPAIRED USERS

[76] Inventor: Phillip H. Winslow, 123 Patton Dr.-Medical Plz., Ponca City, Okla. 74601

[21] Appl. No.: 299,628

[22] Filed: Jan. 23, 1989

[51] Int. Cl.⁴ .............................................. B65D 85/56
[52] U.S. Cl. ...................................... 206/534; 40/310; 40/638; 116/205; 116/DIG. 17; 206/459
[58] Field of Search ................................... 40/310–313, 40/628, 638; 116/205, 308, DIG. 17; 206/459, 534

[56] References Cited

U.S. PATENT DOCUMENTS

| | | | |
|---|---|---|---|
| 889,394 | 6/1908 | Newman | 40/311 |
| 3,334,731 | 8/1967 | Dale | 206/534 |
| 3,537,422 | 11/1970 | Moe | 40/312 |
| 3,675,620 | 7/1972 | Baustin | 116/308 |
| 4,208,983 | 6/1980 | Buckley | 40/312 |

Primary Examiner—Jimmy G. Foster
Attorney, Agent, or Firm—Head & Johnson

[57] ABSTRACT

A system for use by a pharmacist for dispensing pharmaceutical prescription drugs to visually or medically impaired users employing a plurality of sets of containers for receiving prescription drugs therein, each container having on the external surface a visual and tactile indicia in the form of at least one raised symbol, there being one raised symbol for each dosage requirement, the symbols being spaced apart whereby the number of symbols is easily tactilely and visually discernable and the shape of each raised symbol in each set being uniform and distinctive, the shape of each symbol in each set being correlatable with a specific prescription drug and each set including containers having from one to "n" raised symbols thereon where "n" is the maximum dosage rate.

9 Claims, 2 Drawing Sheets

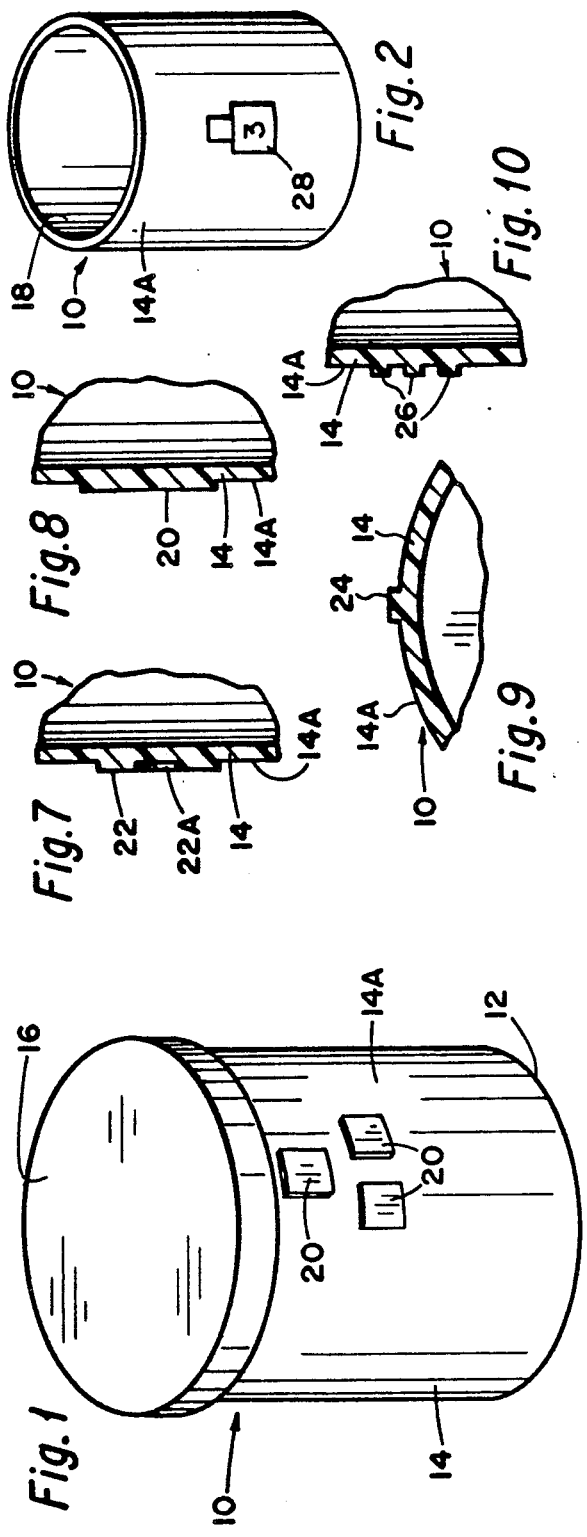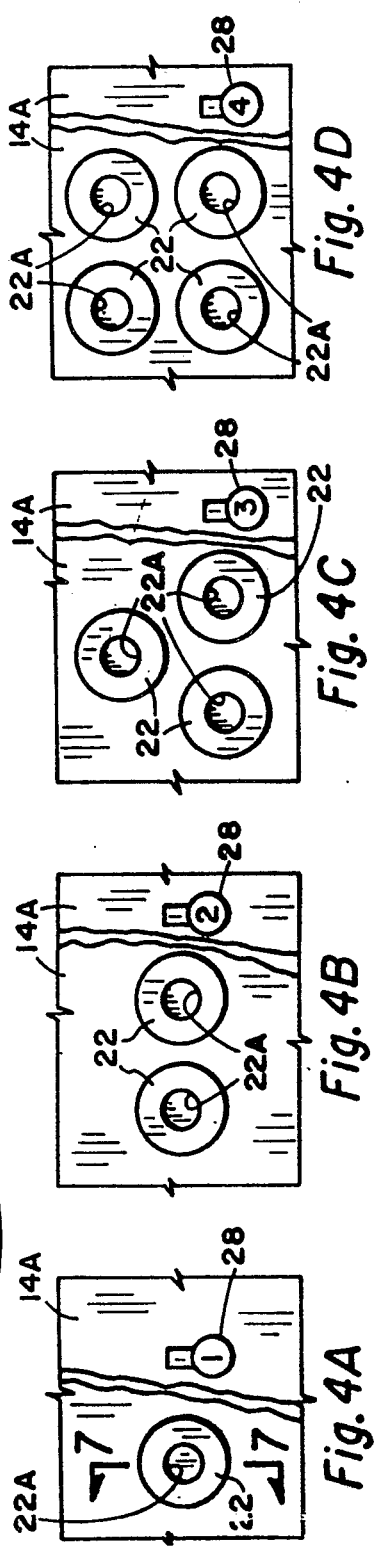

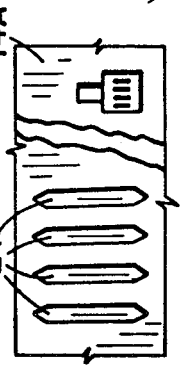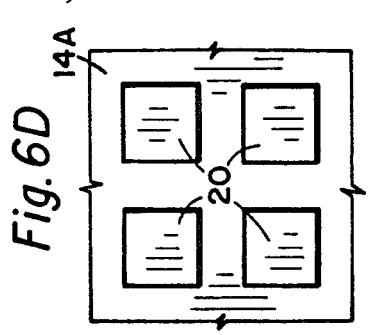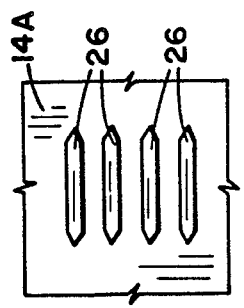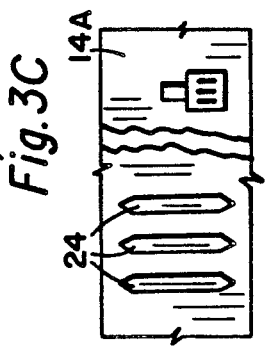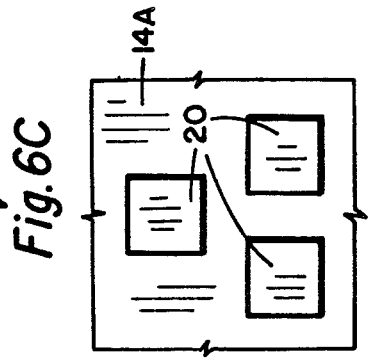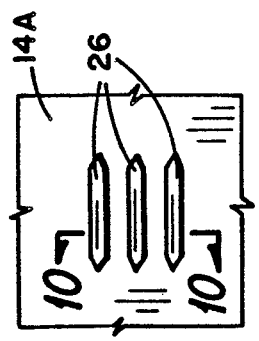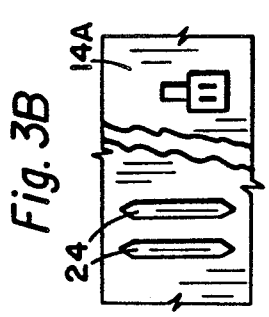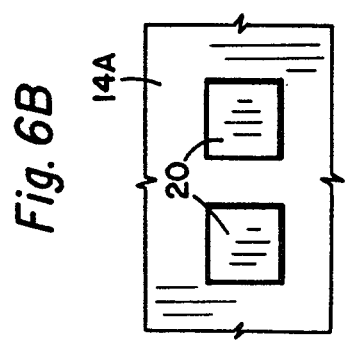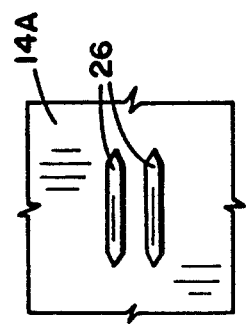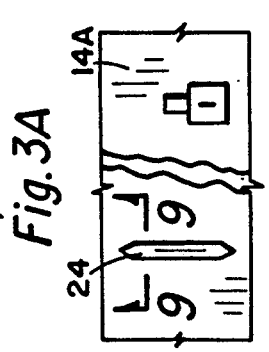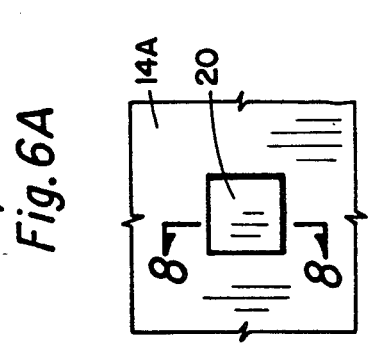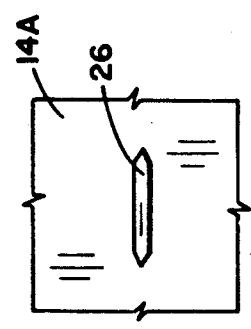

CONTAINER SYSTEM FOR DISPENSING PHARMACEUTICAL PRESCRIPTION TO VISUALLY OR MEDICALLY IMPAIRED USERS

SUMMARY OF THE INVENTION

A major problem in the dispensation of prescription drugs is that a high portion of such drugs are consumed by patients who tend to be either visually or medically impaired or both. It is well-known even outside of the medical profession that for maximum effectiveness, in fact sometimes crucial to effectiveness, prescription drugs must be taken as directed; that is, at a specific dosage rate such as one per day, one with each meal, one with each meal and at bed time, one every four hours, etc. In addition, users of prescription drugs are frequently required to take more than one prescription; and normally the dosage rates for the different prescriptions vary. For the mentally and visually astute, following directions on prescription bottles is not difficult, but for a large number of prescription medicine users it is a serious problem.

The present invention is directed towards a system allowing a pharmacist to dispense drugs in containers in a manner to apprise the visually and/or medically impaired of the difference between drugs and the difference between the dosage requirements. In addition, the system of this invention provides a convenient manner for the pharmacist to record the type of container in which particular prescription drugs are provided to users so as to assist the user in proper use of prescription drugs.

The system employs a plurality of containers for use in dispensing prescription pharmaceuticals. The containers may be of the plastic injection molded cylindrical type, each with a bottom and a cylindrical sidewall and an open top closed by a lid. Each container has thereon at least one visual and tactile indicia in the form of a raised symbol. The raised symbol is of a type wherein the shape is easily determined by feel and/or sight. The symbol may be a circle, a square, horizontal bar, a vertical bar, etc.

The raised symbol is repeated in spaced apart arrangement on the container a number of times, which number is indicative of the prescribed dosage rate.

In the preferred arrangement, each container has, as supplied by the manufacturer, a removable gummed label indicating the shape of the symbol and the number of symbols on the container.

The containers are preferably supplied to a pharmacist as a system consisting of a series of sets of containers. Each set of containers includes a selected symbol and each container in the set has thereon a different number of such selected symbols. For instance, a typical set would include four containers each having a symbol in the form of a raised circle thereon. The first container has one raised circle; the second container, two spaced apart raised circles; the third container, three spaced apart raised circles; and the fourth container, four spaced apart raised circles. The raised symbols are configured so that they are visually easily discernable and are preferably brightly colored so as to contrast with the background color of the container. The symbols are of a size and height to be tactilely easily discernible so that a user can feel of the container and easily recognize two features. The first feature that the user recognizes is the shape of the symbol such as, a square, a circle, a vertical bar, a horizontal bar, etc. This imparts to the user information as to the type of prescription drug contained in the container. Next, the user can readily see and/or feel the number of such symbols. This imparts to the user the dosage rate for the particular prescription drug contained therein. As an example, if the drug is to be taken one per day, then one such symbol will be employed. If the dosage rate is one in the morning and one at bed time, two of such symbols will be employed. If the dosage rate is one before each meal, three of such symbols will be employed. If the dosage rate is one at each meal and one at bed time, four of such symbols will be employed.

Thus, the user can easily see and/or feel indicia differentiating one drug from another and also the dosage rate. For instance, suppose a user is taking prescription A and prescription B—prescription A which must be taken one per day and prescription B must be taken four times per day. The pharmacist will always dispense prescription "A" in a container having a certain symbol, such as a circle, and prescription "B" in a container having a different symbol, such as a square. More specifically, the pharmacist will always, for this user, place prescription A in a container having one circle thereon and prescription B in a container having four squares thereon. The user then learns to correlate each symbol with each specific medication and is reminded of the different dosage rates by the number of symbols on the containers.

The individual containers are preferably supplied to the pharmacist in sets, there being one set for each symbol, and the number of containers in each set being from 1 to "n", "n" being the maximum prescription rate for the specific system. For instance, if the system is designed to employ a dosage rate reminder of from one to four then each set will contain four containers. A typical complete set for use by a pharmacist would contain, as an example, a dispensing tray complete with color tabs distinct to each color symbol and sixteen containers for dispensing prescription pharmaceuticals. When a user purchases a pharmaceutical, the pharmacist selects a symbol to correlate with the particular prescription drug, such as a circle. The pharmacist then selects the container having the number of circles indicative of the prescription rate. The pharmacist can then explain to the user that the circle indicates a certain drug. For instance, if a user is provided with a blood thinner medication, the pharmacist can explain to the user that a container with a circle means that the prescription is the blood thinner. If the same user is also under a prescription for a anti-depressant drug the pharmacist can explain to the user that the anti-depressant drug employs a different symbol, such as a horizontal bar. Each time the pharmacist refills the prescription for this user, a container employing the symbol correlating with the drug is selected; and the container which indicates the prescription rate is selected.

To assist the pharmacist in correlating the use of the container system, each container is preferably supplied by the manufacturer with a removable gummed label thereon indicating the shape of the symbol and the number thereof. The pharmacist can then remove the gummed label from the container before it is handed to the user; and the gummed label can be attached directly to the record kept by the pharmacist. In this way, the pharmacist can always dispense each drug used by a customer with the same symbol; and can utilize containers having the appropriate symbol and the number of symbols thereon corresponding to the dosage rate.

Others have suggested the importance of indicating prescriptions and dosage requirements on the exterior of containers and for reference to suggestions by others as to how this problem may be solved, reference may be had to the following U.S. patents found in a prior art search: U.S. Pat. Nos. 2,066,183; 2,456,155; 2,587,147; 2,713,845; 2,817,451; 3,446,179; 3,537,422; 3,648,647; 4,208,983.

Of the patents found in the search U.S. Pat. No. 4,208,983 to Buckley et al. issued June 24, 1980 for "Container For Symbolically Indicating Pharmaceutical Prescription" is perhaps the closest known prior art. This patent covers the concept of containers having indicia on the exterior thereof which is tactilely discernible, however, the concept revealed in the patent is rather complex and requires the pharmacist to cut away projections extending from the exterior of the container. The system of this patent is, therefore, rather unhandy to utilize and is susceptible to error and mistake. The present invention represents an improvement over the previously known methods of attempting to aid the user of pharmaceutical prescriptions by providing a simple, inexpensive and expedient system for dispensing prescription pharmaceuticals in a way to provide the maximum information to the user in the least complicated manner.

A better understanding of the invention will be had by reference to the following description and claims, taken in conjunction with the attached drawings.

DESCRIPTION OF THE DRAWINGS

FIG. 1 is an external isometric view of a container for dispensing prescription pharmaceuticals employing the principles of this invention.

FIG. 2 is a rear view of the container of FIG. 1 without the lid showing the employment of a removable gummed tag thereon.

FIGS. 3A, 3B, 3C and 3D show fragmentary portions of the exterior of the cylindrical wall of containers showing the employment of a raised square symbol as a visual and tactile indicia with 1, 2, 3, and 4 such symbols being utilized.

FIGS. 4A-4D show the employment of 1, 2, 3, and 4 circles as raised symbols.

FIGS. 5A, 5B, 5C and 5D illustrate the employment of 1, 2, 3, and 4 vertical bars as raised symbols.

FIGS. 6A, 6B, 6C and 6D show the employment of 1, 2, 3, and 4 horizontal bars as raised symbols.

FIG. 7 is a fragmentary cross-sectional view taken along the line 7—7 of FIG. 4A, showing the raised symbol on the exterior surface of the container.

FIG. 8 is a fragmentary cross-sectional view of the wall of a container as taken along the line 8—8 of FIG. 3B showing a square as used as the raised symbol.

FIG. 9 is a fragmentary cross-sectional view taken along the line 9—9 of FIG. 5A, showing the use of a single vertical bar as a raised symbol.

FIG. 10 is a fragmentary cross-sectional view of the wall of a container showing the use of three horizontal bars as the raised symbols.

DESCRIPTION OF THE PREFERRED EMBODIMENT

Referring to FIG. 1, a container employing the principles of this invention is generally indicated by the numeral 10. The container is in the usual shape of a prescription container as typically formed of plastic. The container is an open top type having a bottom 12 and a cylindrical sidewall 14. The container is closed by a cover or lid 16. FIG. 2 shows the container 10 without the lid revealing the opened top 18. The container having elements 12-18 is preferable of the typical type commonly employed for dispensing prescription pharmaceuticals. This invention provides means of modifying the container so as to impart visual and tactile information to the user to reduce the likelihood that a user who is visually and/or medically impaired misuses the prescription sold to him in the container 10.

For this purpose, the container 10 has on the external thereof, and preferably on the external surface 14A of the sidewall an integral, raised, visual and tactilely discernible indicia or symbol generally indicated by the numeral 20. FIG. 1 shows three raised symbols 20 each in the form of a square. A pharmacist would dispense medicine in a container 10 of FIG. 1 to a user. The symbol 20, which is in the form of a raised square, is indicative to the user of a particular prescription drug. In this situation, the symbol, a raised square, would indicate to the user a drug for a specific purpose which may be, as an example, a blood thinner. By this system, the user will be instructed that any container 10 having a raised square symbol thereon contains his prescribed drug thinner medication, and, therefore, both visually and tactilely the user will learn to readily identify his drug thinner medicine.

The number of raised symbols in indicative of the dosage rate. FIG. 1 shows three such raised squares which indicate a dosage rate correlatable with the number 3; such as three times per day or, with each meal, or before each meal, or the like.

The symbols utilized may vary. FIGS. 3A-3D are fragmentary external views of portions of the external sidewall surface 14A of a container showing the use of one symbol in FIG. 3A, two symbols in FIG. 3B, three symbols in FIG. 3C and four symbols in FIG. 3D. The symbols are spaced apart from each other and are of a size, height, and spacing so as to enable the user to easily identify the shape and number, either by sight or feel. To further aid the visually impaired, each of the raised symbols 20 may be colored with a color contrasting with that of the background color of the container. The colors may be very bright and fluorescent.

Various symbols may be employed. For instances, FIGS. 4A-4D show the use of 1, 2, 3, and 4 circles 22. Each of the circles may be formed with a hole or non-raised area 22A therein to augment the identification by feel of the symbol. Further types of symbols may be such as vertical bars 24, as shown in FIGS. 5A, 5B, 5C and 5D or horizontal bars 26 shown in FIGS. 6A, 6B, 6C and 6D.

The drawings thus illustrate four different symbols which may be employed, and it is easily seen that a larger number may be used if necessary. It is believed, however, that in the employment of the system of this invention, normally sets of containers employing four different symbols will suffice for the reason that most users of prescription medicines do not take more than four different kinds of medicines at a time. In addition, the number of indicators of dosage rates is shown to be 1-4. It can be seen that the number may be from 1 to "n", with "n" being the highest dosage rate; however, it is believed that in the typical situation in which pharmaceuticals are dispensed that the proper dosage rate can be indicated to the user by 1 to 4 separate symbols.

FIG. 2 shows the rearward side of the container 10 and shows, on the external cylinder surface 14A thereof, a removable gummed tag 28. The tag 28 has a shape or information thereon indicating the symbol which is integrally formed on the container to which it is attached and the number of such symbols. For instance, the tag can be square when used with square symbols 20 or round when used with round symbols 22. When used with the vertical bars 24 or horizontal bars 26, the symbol can be square with the bars formed thereon either vertically or horizontally and with the number of bars corresponding with the number embossed on the container. The number of symbols can be printed on tag 28, such as the numeral "3" shown thereon indicating that container 10 has 3 squares embossed on the cylindrical sidewall.

The containers of the present invention are preferably sold in sets to pharmacists. A typical complete system would include four sets, with each set containing four containers, for a total of sixteen containers. The pharmacist then selects one of the sixteen containers to dispense a particular drug to a user and assigns a symbol for that drug to that user. The pharmacist explains to the user that that symbol will always indicate to him a particular drug and will explain to the user that the number of the symbols indicate the dosage rate. He then pulls the tag 28 from the container before handing it to the user and places the tag on his record which the pharmacist keeps to indicate the sale of the prescription to the user. In addition, as is the usual practice, the pharmacist will attach a label to the container identifying the patient's name, the drug and the dosage rate. Tag 28 is placed so that it must be removed to provide space for the pharmacist's usual typed label. In this way, each time a user comes to the pharmacist to replace his prescription, the pharmacist will always provide the same drug to the user in a container having the same symbol, and if the dosage rate is the same, the same number of symbols on the container. However, if the dosage rate has been changed by the prescribing physician, a container is selected with the same symbol but with a different number symbols.

There are many thousands of different prescriptions on the market today, but it is not necessary to have a different symbol for each prescription being marketed. It is only necessary to have a limited number of symbols to correspond with the number of prescriptions any one user normally consumes at any one time.

The invention has been illustrated and described in which the raised symbols are integrally formed on the container exterior sidewall surface 14A. This is the preferred embodiment of the invention. The raised symbols could, instead, be placed on lid 16; however, this arrangement is not preferred since the user may inadvertently switch a lid from one container to another (having a different prescription therein). The user is much less likely to change prescriptions from one container to another, therefore, placing the tactile and visual indicia on the container sidewall is much preferred.

The invention has also been illustrated and described in which the raised symbols are integrally formed on the container. Another means of practicing the invention includes affixing the symbols to the container, either sidewall or lid, but preferably sidewall, by use of adhesively applied symbols. Raised and preferably also brightly colored symbols may be made of plastic, or thin metal, with adhesive backing. The adhesive is preferably of the type which, when once applied, makes the symbol very difficult to remove, as contrasted with the easily removed tag 28 previously described.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only be the scope of the attached claim or claims, including the full range of equivalency to which each element thereof is entitled.

What is claimed is:

1. A container for use in dispensing a prescription pharmaceutical to a visually and/or medically impaired user for indicating to the user the pharmaceutical contained therein and the dosage rate, comprising:

an upright, open top container having a bottom, a sidewall having an internal and an external surface, and a removable closure;

the container having on the external surface thereof a visual and tactile indicia in the form of a raised symbol for each dosage requirement, the symbols being spaced from each other whereby the number and shape of the symbols are easily tactile and visually discernible, and the shape of the raised symbol or symbols being uniform and visually and tactilely distinctive whereby the user may determine the pharmaceutical prescription contained in the container by the shape of the symbol or symbols and the dosage rate from the number of symbols; and a removable gummed tag affixed to the container, the tag visually indicating the shape of and the number of raised symbols on the container.

2. A container according to claim 1 wherein said raised symbols are on the said container sidewall external surface.

3. A container according to claim 1 wherein said raised symbols are integrally formed on said containers.

4. A container according to claim 1 wherein said raised symbols are brightly colored with a color contrasting with the color of said container.

5. A container system for use by a pharmacist who keeps a record of the drugs dispensed to visually and/or medically impaired users having means of informing the user of the prescription and dosage requirements comprising:

a plurality of sets of individual upright open top containers, each container having a bottom, a sidewall having an internal and external surface and a removable closure;

each container having on the external surface thereof a visual and tactile indicia in the form of at least one raised symbol, there being one raised symbol for each dosage requirement, the symbols being uniform and spaced apart from each other whereby the number of symbols is easily tactilely and visually discernible, and the shape of each raised symbol in each set being uniform and visually and tactilely distinctive from the symbols of other sets, the shape of each symbol in each set being correlatable with a specific prescription, and each set including containers having differing numbers of symbols from 1 to "n" thereon, "n" being the maximum dosage rate of the system, whereby the pharmacist selects a set having said distinctive symbols thereon for dispensing a specific prescription drug to a specific user and selects from such set of containers a container having the number of raised symbols thereon corresponding to the prescribed dosage rate.

6. The system for use by a pharmacist according to claim 5 including:

a removable gummed tag affixed to each container, the tag indicating the shape of and the number of raised symbols on the container to which it is affixed.

7. The system for use by a pharmacist according to claim 5 wherein said raised symbols are on each said container sidewall external surface.

8. The system for use by a pharmacist according to claim 5 wherein said raised symbols are integrally formed on said containers.

9. The system for use by a pharmacists according to claim 5 wherein said raised symbols are brightly colored with a color contrasting with the color of said containers, there being a different color for each different set of symbols.

* * * * *

UNITED STATES PATENT AND TRADEMARK OFFICE
CERTIFICATE OF CORRECTION

PATENT NO. : 4,895,257

DATED : Jan. 23, 1990

INVENTOR(S) : Winslow

It is certified that error appears in the above-identified patent and that said Letters Patent is hereby corrected as shown below:

Column 6, line 19, change "be" to --by--.

Signed and Sealed this

Twenty-seventh Day of November, 1990

Attest:

HARRY F. MANBECK, JR.

Attesting Officer    Commissioner of Patents and Trademarks